(12) United States Patent
Horie et al.

(10) Patent No.: US 6,549,015 B2
(45) Date of Patent: Apr. 15, 2003

(54) PAIR OF ELECTRODES FOR DETECTING ACIDITY OR BASICITY OF OIL

(75) Inventors: Kazuyuki Horie, Nagoya (JP); Kiwamu Naito, Chita-gun (JP); Hayaki Teramoto, Kariya (JP); Tatsuhiko Nonoyama, Chiryu (JP); Kazushi Asami, Okazaki (JP); Takahiko Yoshida, Okazaki (JP); Hiroshi Ueda, Kariya (JP)

(73) Assignee: Denso Corporation, Kariya (JP)

( * ) Notice: Subject to any disclaimer, the term of this patent is extended or adjusted under 35 U.S.C. 154(b) by 114 days.

(21) Appl. No.: 09/735,460

(22) Filed: Dec. 14, 2000

(65) Prior Publication Data

US 2001/0005137 A1 Jun. 28, 2001

(30) Foreign Application Priority Data

Dec. 14, 1999 (JP) .............................. 11-354812
Nov. 6, 2000 (JP) ........................ 2000-337839

(51) Int. Cl.[7] ...................... G01N 27/416; G01N 27/26; G01N 31/22; G01R 27/08
(52) U.S. Cl. ...................... 324/438; 324/698; 204/433; 204/435; 436/163
(58) Field of Search ................ 324/438, 698, 324/444, 71.1; 204/435, 433, 196.38, 292; 436/163; 205/775, 787.5

(56) References Cited

U.S. PATENT DOCUMENTS

| | | | | |
|---|---|---|---|---|
| 3,957,613 A | * | 5/1976 | Macur | 204/412 |
| 5,146,169 A | * | 9/1992 | Morishita et al. | 324/438 |
| 5,393,616 A | * | 2/1995 | Mori et al. | 420/900 |
| 6,277,305 B1 | * | 8/2001 | Gorge et al. | 148/674 |
| 6,348,667 B2 | * | 2/2002 | Baumann et al. | 219/68 |

FOREIGN PATENT DOCUMENTS

| | | |
|---|---|---|
| JP | 62-25250 | 3/1987 |
| JP | 6-201649 | 7/1994 |

* cited by examiner

Primary Examiner—N. Le
Assistant Examiner—Anjan K. Deb
(74) Attorney, Agent, or Firm—Nixon & Vanderhye P.C.

(57) ABSTRACT

In a pair of electrodes where a potential difference is changed in accordance with acidity or basicity of oil, a reference electrode is made of cobalt or a cobalt alloy, and a sensitive electrode is made of tungsten or a tungsten alloy. The sensitive electrode is used in combination with the reference electrode. Accordingly, it is possible to provide a pair of electrodes for detecting the acidity or the basicity of the oil which use a novel electrode material not hazardous to the environment and at the same time, suited for use in a semiconductor fabrication technique.

6 Claims, 2 Drawing Sheets

PAIR OF ELECTRODES FOR DETECTING ACIDITY OR BASICITY OF OIL

CROSS-REFERENCE TO RELATED APPLICATION

This application is related to and claims priority from Japanese Patent Applications No. Hei. 11-354812 filed on Dec. 14, 1999 and No. 2000-337839 filed on Nov. 6, 2000, the contents of which are hereby incorporated by reference.

BACKGROUND OF THE INVENTION

1. Field of the Invention

The present invention relates to a pair of electrodes for detecting acidity or basicity of oil, which undergo a change in a potential difference in accordance with the acidity or basicity in oil. More particularly, the present invention relates to a reference electrode and a sensitive electrode constructing the pair of electrodes.

2. Description of the Related Art

Various kinds of oils such as fuel oil, working oil, quenching oil and lubricating oil have industrially been used. However, they are known to show a gradual increase in their acidity due to oxidation by air, accumulation of a combustion product or the like during storage or use and eventually undergo corrosion or an undesirable deterioration of their initial performances. It is therefore a matter of great importance in the maintenance of oil to detect its deterioration quickly and accurately.

For detecting such a deterioration of oil, for example, in U.S. Pat. No. 5,146,169, JP-A-6-201649 or JP-A-62-25250, a pair of electrodes are constructed by a sensitive electrode in which a potential difference varies in response to the acidity or basicity of the oil, and a reference electrode which is different from the sensitive electrode in an inclination degree representing a potential change.

Further, in a pair of electrodes as described in JP-A-62-25250, Pb (lead) is employed as a reference electrode for a pair of electrodes. Because Pb is however a substance hazardous to the environment, the use of Pb as a reference electrode is not desired.

On the other hand, as a sensitive electrode to be used in combination with a reference electrode, SUS (stainless) is conventionally known. In this case, an electrode portion is formed into a plate like, and its size inevitably becomes large, thereby deteriorating arrangement properties. In order to overcome such a problem, a size reduction of the electrode portion by using a semiconductor fabricating technique such as screen printing, deposition or sputtering is considered, but metals such as SUS are not suited for the fabrication technique.

SUMMARY OF THE INVENTION

In view of the foregoing problems, it is an object of the present invention to provide a pair of electrodes for detecting acidity or basicity of oil, which are made of a novel electrode material not hazardous to the environment but suitable for use in a semiconductor fabrication technique, and to provide a reference electrode and a sensitive electrode which can suitably used for the pair of electrodes.

According to the present invention, in a pair of electrodes where a potential difference is changed in accordance with acidity or basicity of oil, a reference electrode is made of cobalt or a cobalt alloy, and a sensitive electrode is made of tungsten or a tungsten alloy. The sensitive electrode is used in combination with the reference electrode. The cobalt or the cobalt alloy and the tungsten or the tungsten alloy are not substances hazardous to the environment, and it is possible to perform the manufacture of the electrodes by screen printing, deposition or sputtering. Accordingly, it is possible to provide a pair of electrodes for detecting the acidity or the basicity of the oil which use a novel electrode material not hazardous to the environment and at the same time, suited for use in a semiconductor fabrication technique.

Alternatively, the sensitive electrode combined with the reference electrode is made of titanium or a titanium alloy. In this case, the sensitive electrode has an oxide film on the surface thereof, and a thickness of the oxide film is in a range of 7–80 nm. Therefore, sensitive performance of the sensitive electrode can be improved. Accordingly, the same effect described above can be obtained.

BRIEF DESCRIPTION OF THE DRAWINGS

Additional objects and advantages of the present invention will be more readily apparent from the following detailed description of a preferred embodiment when taken together with the accompanying drawings, in which.

DETAILED DESCRIPTION OF THE PRESENTLY PREFERRED EMBODIMENTS

A preferred embodiment of the present invention will be described hereinafter with reference to the accompanying drawings.

In a pair of electrodes which undergo a change in a potential difference in accordance with the acidity or basicity of oil, a simple substance of cobalt (Co) is used as a reference electrode, while a simple substance of tungsten (W) is used as a sensitive electrode in combination with the reference electrode.

Although no particular limitation is imposed on each of the pair of electrodes, it can be formed, for example, into a comb shape as an ordinarily employed electrode. Specifically, the pair of electrodes are manufactured by sputtering Co or W to form its film on a surface of a substrate made of alumina or a resin or a substrate made of Si or Sus having an insulator formed thereon, and thereafter, patterning them into a comb shape by photolithography, for forming a reference electrode and a sensitive electrode, respectively. Further, the comb-shaped portion of the reference electrode is made opposite to that of the sensitive electrode to be engaged with that of the sensitive electrode. Between the reference electrode and the sensitive electrode, the potential difference corresponding to the acidity or the basicity of the oil is detected as an output potential (sensor output), so that a deterioration of the oil can be detected.

Next, investigation examples of the performance of the sensitive electrode and the reference electrode of the embodiment, for detecting the acidity or the basicity of an oil, will be now described. The sensitive electrode and the reference electrode, each of which is formed into a strip like (e.g., 5 cm in length, 3 cm in width, 2 cm in thickness), are-dipped in plural solutions (test solutions) which are difference in a deterioration degree. The test solutions are obtained by diluting to 25 folds each of lubricating oils for a gasoline engine with a solvent (a 50:49.5:0.5 mixture of toluene, 2-propanol and water) as prescribed in JIS K2501.

Figure 1:
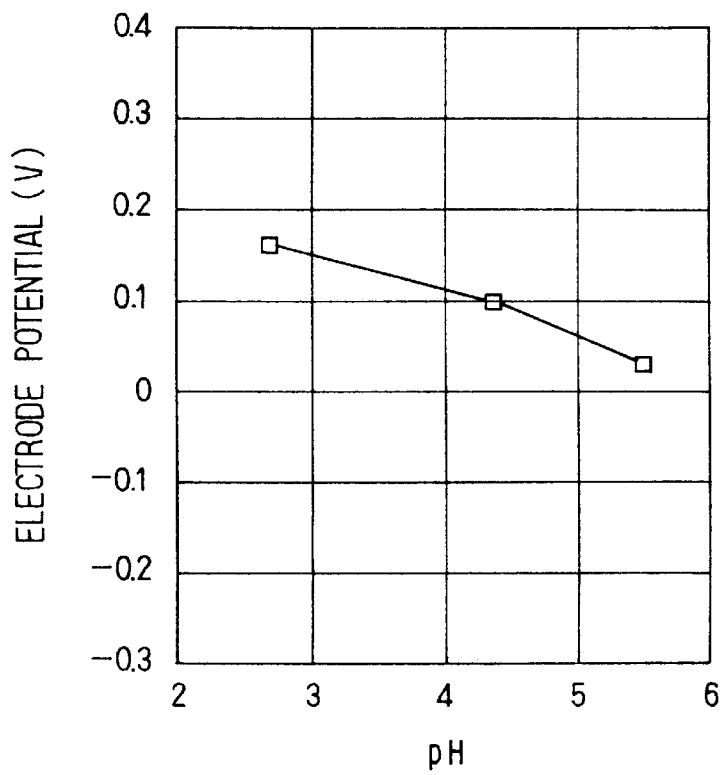
FIG. 1 is a characteristic view of a sensitive electrode (W) actually measured with a silver/silver chloride electrode as a standard, according to a preferred embodiment of the present invention.
Figure 2:
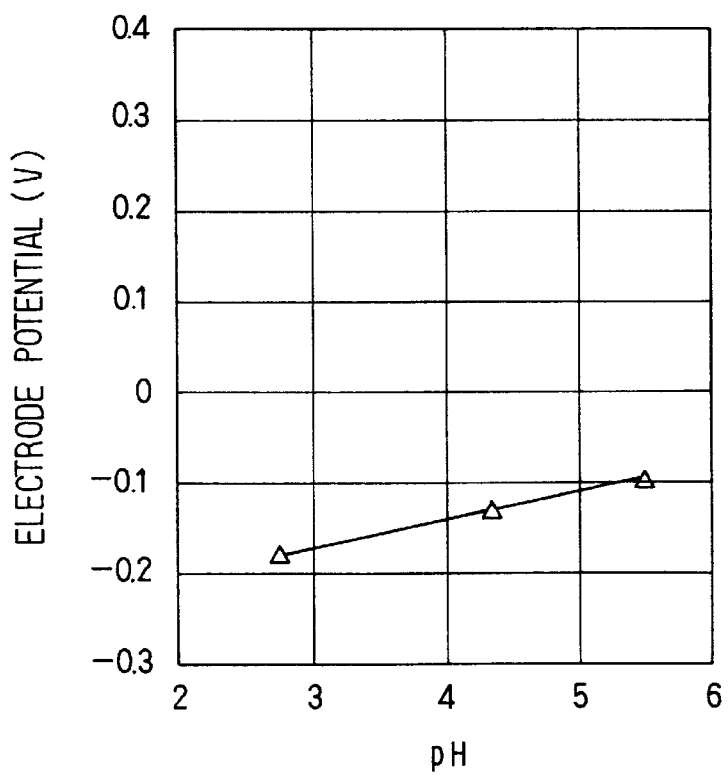
FIG. 2 is a characteristic view of a reference electrode (Co) actually measured with the silver/silver chloride electrode as a standard, according to the preferred embodiment.

Then, the sensitive electrode (W) or the reference electrode (Co) of this embodiment is combined with a silver/silver chloride electrode which is a well-known reference electrode. In each of the test solutions, for example, a distance between the sensitive electrode or the reference electrode and the silver/silver chloride electrode disposed opposite thereto is set at about 3 cm, and the potential difference between them is measured using a potentiometer at room temperature. FIG. 1 shows a relationship between the potential difference (electrode potential, unit V) of the sensitive electrode W, actually measured with the silver/silver chloride electrode as a standard, and the pH of the test solutions as measured by a pH meter. FIG. 2 shows a relationship between the potential difference (electrode potential, unit V) of the reference electrode Co, actually measured with the silver/silver chloride electrode as a standard, and the pH of the test solutions.

As shown in FIG. 1, the potential difference (electrode potential) of the W electrode has a negative inclination in response to a change (an increase) of pH of the test solution. Therefore, the W electrode exhibits a satisfactory performance as a sensitive electrode. As shown in FIG. 2, the potential difference (electrode potential) of the Co electrode has a positive inclination or flat line, contrary to that of the W electrode, in response to a pH change (an increase) of the test solution. Therefore, the Co electrode exhibits a satisfactory performance as a reference electrode. The reference electrode (Co) and the sensitive electrode (W) have opposite inclinations each other in response to a pH change. However, even if both reference electrode and sensitive electrode exhibit similar inclinations in response to the PH change, they can be employed at least when their inclination degrees of the electrode potential relative to the PH change are different.

Figure 3:
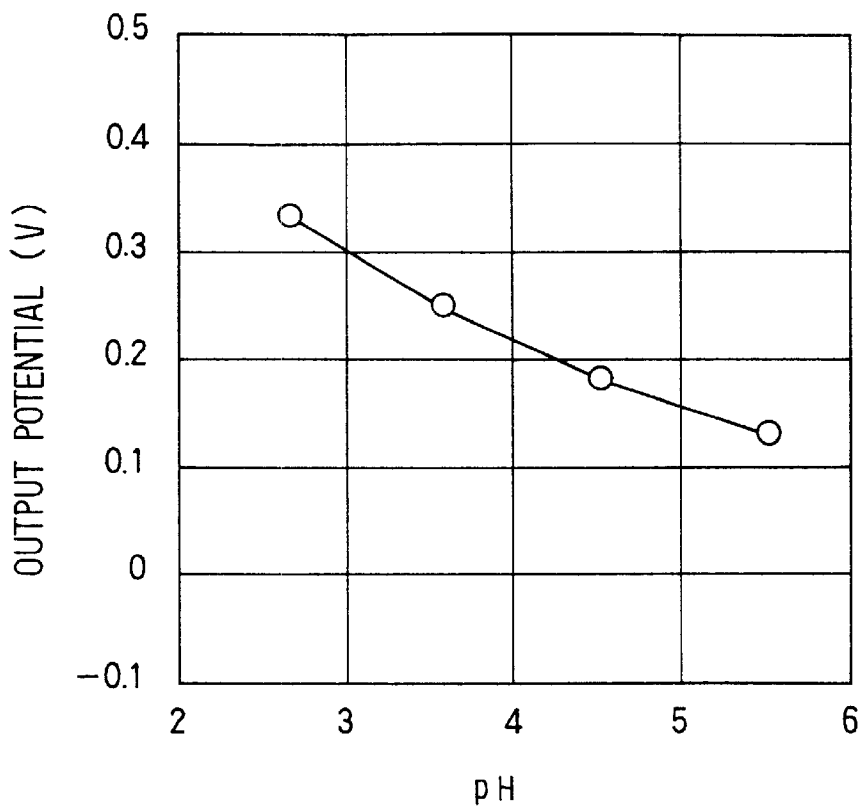
FIG. 3 is a characteristic view of an output potential using a pair of Co and W electrodes, according to the preferred embodiment.

The Co electrode as the reference electrode and the W electrode as the sensitive electrode are used in combination, and the potential difference between the pair of Co and W electrodes is detected for detecting the acidity or the basicity of oil, so that output potential (sensor output) corresponding to the acidity or the basicity of the oil is obtained. FIG. 3 shows the characteristics of the output potential (unit V) of the oil determined using the pair of Co and W electrodes. By using this pair of Co and W electrodes, the acidity or the basicity of the oil can be detected accurately, as shown in FIG. 3.

As the sensitive electrode of the embodiment, not only that formed of a simple substance of W but also that formed of an alloy of W and another metal (such as Ti, Pt or Ag) can be employed. As the reference electrode, not only that formed of a simple substance of Co but also that formed of an alloy of Co and another metal (such as Cu or Ni) can be employed. Even if the sensitive electrode or the reference electrode is formed of an alloy of W or Co, an output potential corresponding to the acidity or the basicity of the oil can be available by measuring the potential difference between both the electrodes.

As described above, in this embodiment, the reference electrode is formed of Co or a Co alloy, while the sensitive electrode is formed of W or a W alloy. These Co, Co alloy, W and W alloy are not substances hazardous to the environment and permit the manufacture of the electrode portion by screen printing, deposition or sputtering. According to the embodiment, it is possible to provide a pair of electrodes for detecting the acidity or the basicity of the oil which use a novel electrode material not hazardous to the environment and at the same time, suited for use in a semiconductor fabrication technique. That is, the reference electrode and the sensitive electrode described above can be suitable for the pair of electrodes for detecting the acidity or the basicity of the oil.

Compared with the use of an electrode material, such as stainless, the pair of electrodes of this embodiment can be freely formed. For example, the comb-shaped reference electrode and the comb-shaped sensitive electrode can be formed on the above-exemplified substrate by using the semiconductor fabrication technique. As a result, in this embodiment, a pair of electrodes having a reduced size and moreover, good arrangement properties can be provided.

Although the present invention has been fully described in connection with the preferred embodiment thereof with reference to the accompanying drawings, it is to be noted that various changes and modifications will become apparent to those skilled in the art.

For example, the sensitive electrode can be formed of titanium (Ti) or an titanium arrow. In this case, it is preferred to have a surface on which an oxide film having a thickness not less than 7 nm but not greater than 80 nm is formed by thermal oxidation or the like method. The sensitive electrode of titanium or a titanium arrow with an oxide film on its surface has improved sensitivity.

Figure 4:
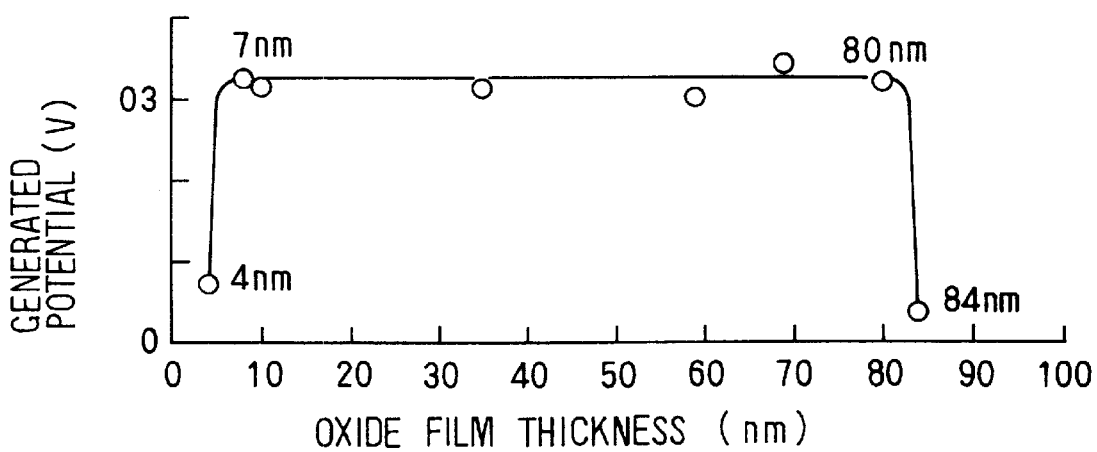
FIG. 4 is a view showing a relationship between a thickness of an oxide film of a sensitive electrode made of Ti or a Ti alloy and a potential generated at the electrode, according to a modification of this embodiment.

FIG. 4 illustrates a relationship between a thickness (nm) of an oxide film formed on the sensitive electrode made of Ti (or a Ti alloy) and a potential (V) generated at the electrode. As shown in FIG. 4, it is understood that the desirous potential can be generated at the sensitive electrode made of Ti (or a Ti alloy) when the thickness of the oxide film formed on the surface thereof is not less than 7 nm but not greater than 80 nm.

It is also possible to form a pair of electrodes by using, in combination, a reference electrode made of Co or a Co alloy, and a sensitive electrode made of an electrode material (such as Ti, Pt or Ag). The electrode material such as Ti, Pt, or Ag is not hazardous to the environment, and is suited for use in a semiconductor fabrication technique. Alternatively, a pair of electrodes can be formed using, in combination, a reference electrode made of an electrode material (such as Cu or Ni) which is not hazardous to the environment and is suited for use in a semiconductor fabrication technique, and a sensitive electrode made of W or a W alloy.

Such changes and modifications are to be understood as being within the scope of the present invention as defined by the appended claims.

What is claimed is:

1. A pair of electrodes for detecting acidity or basicity of oil, the pair of electrodes are constructed by a reference electrode made of cobalt or a cobalt alloy; and a sensitive electrode made of tungsten or a tungsten alloy, the sensitive electrode being used in combination with the reference electrode, wherein a potential difference between the sensitive electrode and the reference electrode is changed in accordance with the acidity or the basicity of the oil.

2. A reference electrode used in combination with a sensitive electrode, for a pair of electrodes where a potential difference is changed in accordance with acidity or basicity of oil, wherein the reference electrode is made cobalt or a cobalt alloy.

3. The reference electrode according to claim 2, wherein:

the sensitive electrode combined with the reference electrode is made of titanium or a titanium alloy;

the sensitive electrode has an oxide film on the surface thereof; and a thickness of the oxide film is in a range of 7–80 nm.

4. The reference electrode according to claim 2, wherein the sensitive electrode combined with the reference electrode is made of tungsten or a tungsten alloy.

5. A sensitive electrode used in combination with a reference electrode, for a pair of electrodes where a potential difference is changed in accordance with acidity or basicity of oil, wherein:

the sensitive electrode is made of titanium or a titanium alloy;

the sensitive electrode has an oxide film on the surface thereof; and a thickness of the oxide film is in a range of 7–80 nm.

6. A detecting device for detecting acidity or basicity of oil, the device comprising:

a first electrode made of one of cobalt and a cobalt alloy; and a second electrode made of one of tungsten and a tungsten alloy, the second electrode being used in combination with the first electrode, wherein a potential difference between the first electrode and the second electrode is changed in accordance with the acidity or the basicity of the oil.

* * * * *

UNITED STATES PATENT AND TRADEMARK OFFICE
CERTIFICATE OF CORRECTION

PATENT NO. : 6,549,015 B2
DATED : April 15, 2003
INVENTOR(S) : Horie et al.

It is certified that error appears in the above-identified patent and that said Letters Patent is hereby corrected as shown below:

<u>Title page,</u>
Item [73], the assignee information should appear as follows:

-- [73]   Assignees:   Denso Corporation, Kariya-city (JP)
   Nippon Soken, Inc., Nishio-city (JP) --

Signed and Sealed this

Second Day of September, 2003

JAMES E. ROGAN
*Director of the United States Patent and Trademark Office*